United States Patent [19]

Sielaff et al.

[11] 4,016,864
[45] Apr. 12, 1977

[54] BLOOD GAS CATHETER
[75] Inventors: Ulrich Sielaff; Wilfried R. Peickert, both of Madison, Wis.
[73] Assignee: Airco, Inc., Montvale, N.J.
[22] Filed: Sept. 8, 1975
[21] Appl. No.: 611,473

Related U.S. Application Data
[63] Continuation-in-part of Ser. No. 493,939, Aug. 1, 1974, abandoned.
[52] U.S. Cl. .............................. 128/2 G; 23/230 B; 23/254 R; 128/2 F; 128/2 L
[51] Int. Cl.[2] ............................................ A61B 5/00
[58] Field of Search ............ 128/2 L, 2 E, 2 G, 2 F, 128/2 R, 348, 214.4; 23/230 B, 232 C, 254 R; 73/421.5 R, 23 R, 23.1

[56] References Cited
UNITED STATES PATENTS

| | | | |
|---|---|---|---|
| 3,512,517 | 5/1970 | Kadish et al. | 128/2 E |
| 3,572,315 | 3/1971 | Cullen | 128/2 E |
| 3,640,269 | 2/1972 | Delgado | 128/2 R |
| 3,658,053 | 4/1972 | Fergusson et al. | 128/2 G |
| 3,664,178 | 5/1972 | Spergel et al. | 128/2 E |
| 3,824,157 | 7/1974 | Macur | 128/2 E |

OTHER PUBLICATIONS

Med. & Biol. Engng., vol. 8, No. 2, pp. 111-128, (1970).
Journ. Of Thoracic & Cardiovascular Surg., vol. 62, No. 6, Dec. 1971, pp. 844-850.

Primary Examiner—Kyle L. Howell
Attorney, Agent, or Firm—Roger M. Rathbun; Edmund W. Bopp; H. Hume Mathews

[57] ABSTRACT

An instrument for withdrawing equilibrated blood gases in vivo, which comprises a tubular gas permeable membrane inserted through a cannular into the blood stream. In preferred form, the tubular membrane comprises a continuous conduit in contact with the blood. An inlet supply gas terminal is constructed for connection to a carrier gas source, and an outlet gas terminal, for connection to an appropriate analyzer. In preferred forms of the invention, a heater maintains the equilibrated gases at above normal body temperature as they pass to the analyzer; and a port is provided for drawing blood samples from the area being analyzed without dislodging the catheter.

18 Claims, 9 Drawing Figures

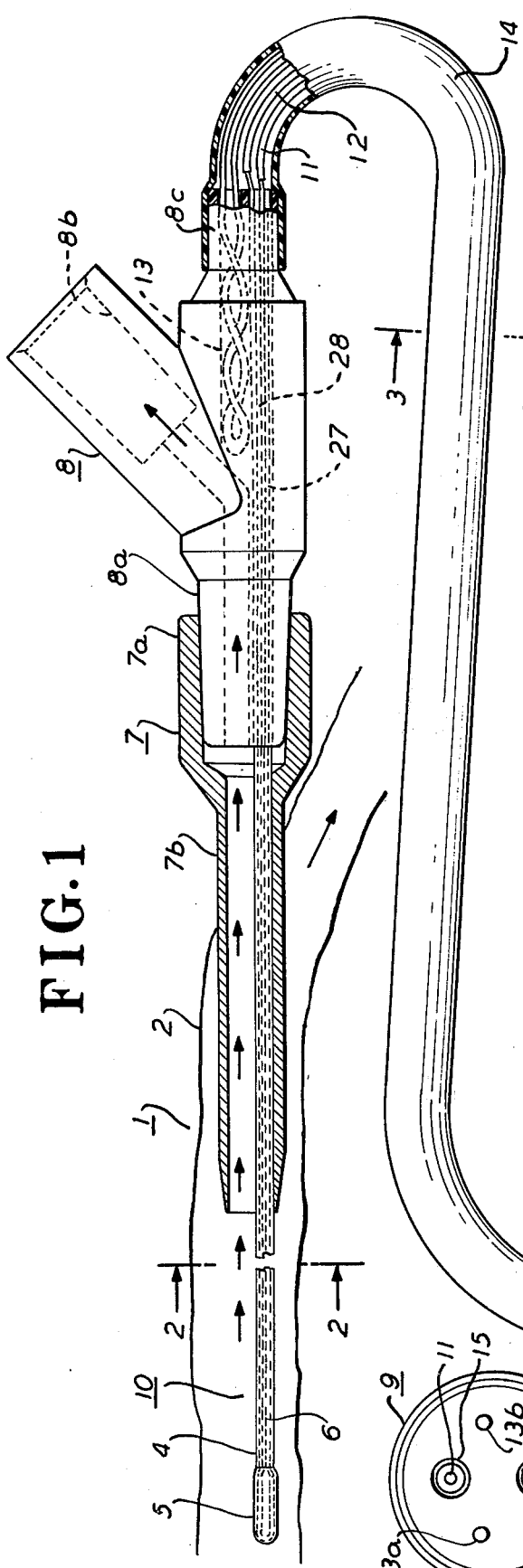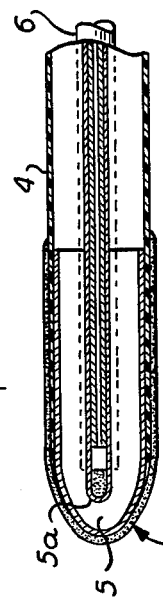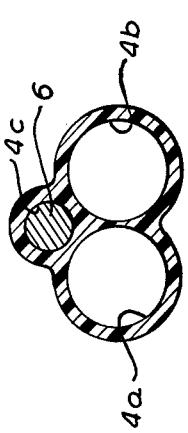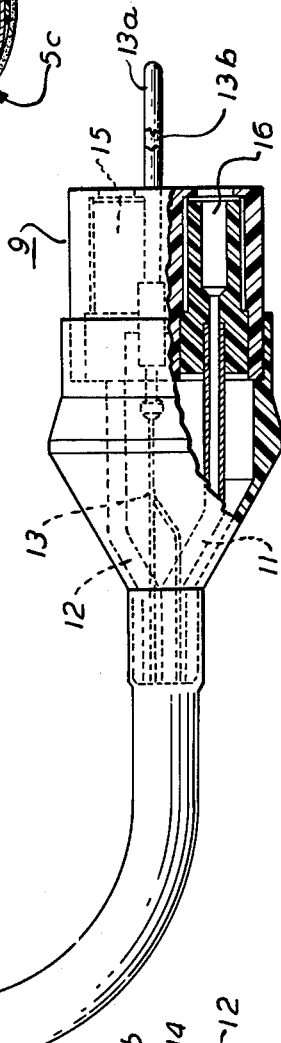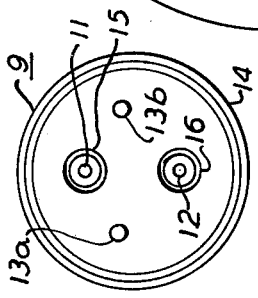

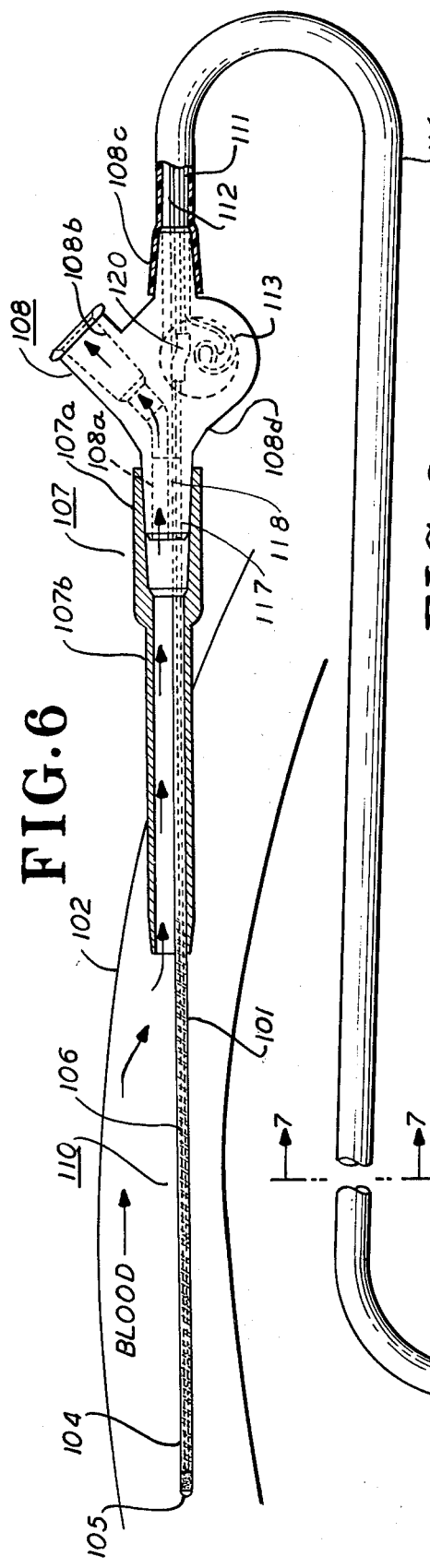
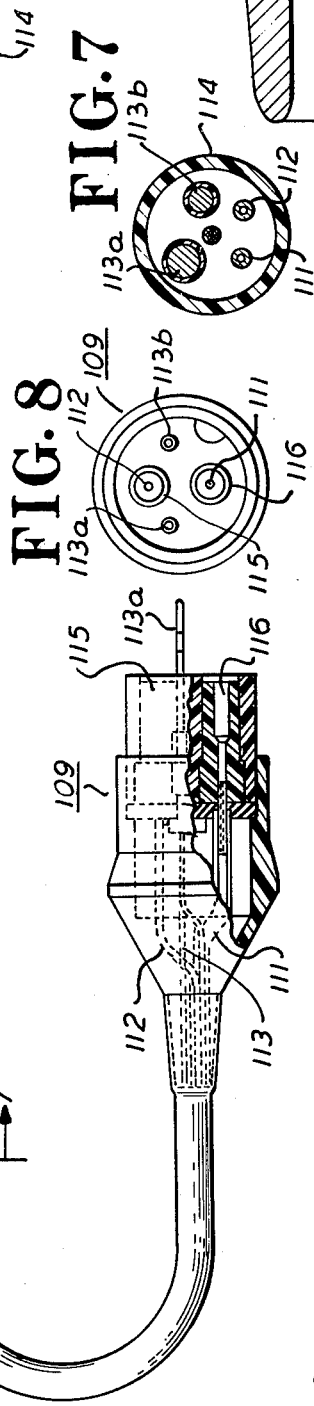
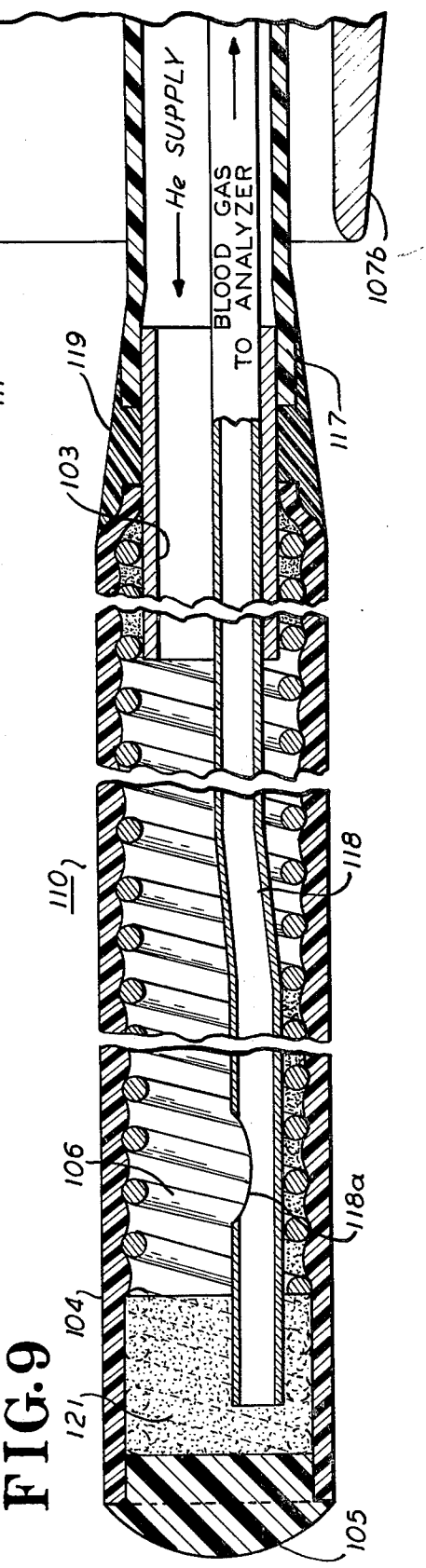

4,016,864

BLOOD GAS CATHETER

BACKGROUND OF THE INVENTION

This is a Continuation-in-Part of application Ser. No. 493,939, filed Aug. 1, 1974, now abandoned.

This relates in general to catheters, and more specifically to instruments for withdrawing blood gases from the blood vessel of a subject in vivo.

Blood gases have been detected and measured in vivo by a variety of electronic means. The most successful have been variations of the polarographic electrode for measurement of oxygen, and modified pH electrodes for measurement of carbon dioxide. Oxygen, $CO_2$ and other dissolved blood gases have also been detected and measured in the prior art on the basis of their flow rates into an evacuated gas permeable membrane-tipped catheter in contact with the blood. The prior art systems of the latter type are specifically designed to operate with mass spectrometers. Blood gases pass through a small membrane area at the distal end of the catheter and are drawn to the mass spectrometer at a rate proportional to their partial pressure in the blood. The mass spectrometer determines the relative number of each type of gas molecule passing into the system and thus, with proper calibration, the partial pressures in the blood may be indirectly determined.

All of the prior art methods described here rely on the rate of gas diffusion through a membrane to indicate the partial pressures of the gases in the blood. In such measurements, a steady state diffusion rate is reached which is a function of the membrane thickness, the membrane surface conditions, blood velocity, temperature, etc., which parameters are either unknown or difficult to control. The combined effects of these variables on the overall measuring system can only be overcome by calibrating each system after it is in place in the artery. It is also known that these variables may change during the time that a continuous blood gas measurement is being made. The membrane probes are known to change position within the blood stream, resulting in varied blood flow conditions which can alter the gas diffusion rates. The membrane characteristics will also change under the effect of protein buildup on their surfaces, thus changing the diffusion rates. It is thus necessary to calibrate such systems frequently during their use to account for the changes in gas diffusion rates which naturally occur. Each calibration necessitates the extraction of a blood sample for gas pressure determination with an in vitro instrument.

Application Ser. No. 493,938 of U. Sielaff, W. R. Peickert and D. Brinkman, filed on Aug. 1, 1974, now abandoned, and continuation application Ser. No. 593,606, filed on the above-named application on July 7, 1975, now U.S. Pat. No. 3,983,864, disclosures of each of which is made a part hereof by reference, relate to a method and apparatus for withdrawing equilibrated blood gas samples in vivo. In accordance with the invention therein disclosed, a highly diffusible tubular membrane which, in preferred embodiment, takes the form of the catheter disclosed in the instant application, is introduced percutaneously into the blood stream and serves as a conduit for carrier gas and blood gases. Equilibration is allowed to occur for a preselected period between the blood gases and the carrier gas through the membrane. The equilibrated gas is then removed from the diffusible membrane to another area for analysis by displaced volume or reduced pressure. A corresponding volume of carrier gas is replaced in the diffusible tubular membrane from an inlet supply. This system is well adapted for use with the gas chromatograph type of analyzer which is simpler and more economincal than the mass spectrometry previously used in combination with prior art systems employing diffusible membranes.

SHORT DESCRIPTION OF THE INVENTION

A particular object of the present invention is to provide an improved catheter for equilibrating and withdrawing blood gases from the blood vessels of a living subject and, more particularly, a catheter having a maximum surface for diffusion of gases in the blood in large enough volumes to meet the requirements for analysis in a gas chromatographic type of analyzer.

Another object of the present invention is to provide a catheter for in vivo blood gas measurements in which blood samples from the immediate analyzed area may be withdrawn without removal or disturbance of the catheter.

A further object of the invention is to provide a catheter system which maintains the equilibrated gas sample at a controlled temperature as it is conveyed to the analyzer.

These and other objects are realized in accordance with the present invention in an instrument for withdrawing equilibrated blood gases in vivo comprising a catheter including a highly gas permeable tubular membrane, which is designed to be inserted through a cannula into a blood vessel of the subject. In one embodiment the tubular membrane comprises a pair of parallel lumens which are connected at their distal ends by a U-tube permitting return flow, and a slightly smaller lumen parallel to the other two which houses a thin stiffening wire soldered to the U-tube at the distal end of the membrane. Another embodiment comprises a tubular membrane supported internally by a stainless steel coil. Carrier gas is supplied to the proximal end of the tubular membrane, which is closed at the distal end, the return flow of equilibrated carrier gas passing through an internal non-diffusible tube disposed parallel to the axis of the tubular membrane.

In each of the embodiments, a three-way coupling, connected to the proximal end of the tubular membrane, includes a port for the taking of blood samples.

The input and output connections to the tubular membrane connect to substantially non-diffusible tubular members enclosed in an insulating outer tube. The ends of the tubular members are connected to a plug which contains terminals for the carrier gas source, and gas analyzer, respectively. The non-diffusible members are in close contact with a pair of parallel heater wires which serve to maintain the equilibrated gases at above normal temperature as they pass to the gas analyzer.

A particular advantage of the catheter designs of this invention is that they provide permeable membranes of maximum surface area for diffusion of gases in the blood in sufficient volumes for chromatographic analysis. Other advantages of the present catheter designs are their flexibility, that blood samples may be withdrawn from the immediate analyzed area without removing or disturbing the catheter, and that the blood gases are maintained at uniform temperature as they are conveyed to the gas analyzer.

Other objects, features, and advantages of the invention will be apparent from a study of the drawings with reference to the detailed specification hereinafter.

SHORT DESCRIPTION OF THE DRAWINGS

FIG. 1 is a view partially in longitudinal section of a catheter assemblage, in accordance with one embodiment of the present invention employing a tri-lumen tubular membrane.

FIG. 2 is a cross-sectional view showing the tubular membrane portion of the catheter of FIG. 1 along a plane indicated by the arrows 2—2.

FIG. 3 is a cross-sectional view showing the connecting conduit members between the tubular membrane coupling and terminal plug along the plane 3—3 of FIG. 1.

FIG. 4 is an end view of the terminal plug 9 of FIG. 1.

FIG. 5 is an enlarged view of the distal end of the catheter shown in FIG. 1 showing details of the U-tube configuration of the tri-lumen membrane.

FIG. 6 shows, partly in longitudinal section, another embodiment of the catheter of the present invention in which a tubular membrane having an internal return tube impermeable to gas, is supported internally by a stainless steel coil.

FIG. 7 is a cross-section taken through the plane 7—7 of FIG. 6.

FIG. 8 is an end elevation of the plug 109.

FIG. 9 is an enlarged detailed longitudinal section of the distal end of the catheter of FIG. 6.

DETAILED DESCRIPTION OF THE DRAWINGS

Referring to FIGS. 1 through 5, and 6 through 9, there are shown two different embodiments of the present invention, each comprising an instrument for detecting dissolved gases in the blood and withdrawing such gas samples intermittently from the blood, hereinafter called blood gas catheters 1, and 101, respectively. Referring specifically to FIG. 1, gas permeable tri-lumen tubular membrane 4 is interposed through the walls of a blood vessel 2, say an artery, into the bloodstream through a cannula 7. Tri-lumen gas permeable tubular membrane 4 may comprise, for example, a methyl-vinyl-polysiloxane polymer with fumed silica filler, for rigidity. The material of membrane 4 is so characterized that it is diffusible to gases, but substantially indiffusible to liquids, such as blood.

The criteria for selecting semi-permeable membranes for the purposes of the present invention are: (1) the compatability with blood must be good, so that the membrane does not contaminate the blood, or cause a build-up of blood, or blood components on the membrane; and (2) the permeability rate of diffusion for the measured gases through the membranes must be high in order to collect the maximum volume of gas in the minimum time.

In the case of a preferred material, dimethyl silicone, the literature indicates that diffusion takes place through the membrane according to the following formulations:

For Oxygen:

$$R = 50 \times 10^{-9} [V\tau/(tA \Delta P)]$$

where $R$ = permeability of the gas permeable membrane;
$V$ = volume in cm.$^3$ of dissolved gas;
$\tau$ = wall thickness of the membrane in cm.;
$t$ = time in seconds;
$A$ = active area of membrane in cm.$^2$;
$\Delta P$ = differential partial gas pressure across the membrane measured in cm. of mercury.

For Carbon Dioxide:

$$R = 300 \times 10^{-9} [V\tau/(tA\Delta P)]$$

where the parameters enclosed in the brackets are the same as for oxygen, indicated above.

For the preferred catheter embodiment, this results in an initial gas exchange rate at normal or typical physiological conditions, of $1.5 \times 10^{-3}$ cubic centimeters of oxygen per second and $4.0 \times 10^{-3}$ cubic centimeters of carbon dioxide per second. For the purposes of this specification and claims hereinafter, "normal or typical physiological conditions" will be defined as blood gas levels in the subject in which the partial pressure of oxygen, $PO_2$=90 milimeters of mercury; and the partial pressure of carbon dioxide, $PCO_2$=40 milimeters of mercury.

It will be understood that in addition to dimethyl silicone, other materials have been found suitable for the purposes of the present invention. Other suitable materials include methyl-vinyl-polysiloxane, polycarbonate/silicone copolymers, expanded tetrafluoroethylene (TEFLON), and expanded polypropylene. In each case the wall thickness of the material is adjusted to maximize the rate of diffusion.

Cannula 7 is a conventional commercially available cannula having a hollow cylindrical mouth 7a, and a distal end comprising a plastic tube 7b, which is tapered for insertion through the skin and into blood vessel 2. The tubular portion 7b of the cannular accommodates the proximal end of tubular membrane 4 coaxially guiding it into place in the vessel 2, where it may remain semipermanently, even when the measuring sytem is disconnected.

The cross-sectional geometry of the tubular membrane 4 may be varied; but the tri-lumen membrane construction has been chosen in the embodiment under description to expose maximum surface area of the membrane in the blood vessel. The structure is shown more clearly in the sectional view of FIG. 2. The two larger lumens 4a, 4b are each about 0.011 inch in diameter and are connected by means of a U-shaped stainless steel or nickel tube 5, thus permitting a reversal in the direction of gas flow from one lumen to the second lumen. The small 0.006 inch diameter lumen 4c accommodates a stainless steel wire 6 of 0.006 inch diameter which is soldered at its distal end in a smooth joint 5a to the inner curve of the stainless steel U-shaped tube 5. An adhesive coating 5c, preferably dimethylsilicone, surrounds and protects the end of the U-tube and provides a smooth transition between the U-tube and the membrane 4. The wire 6 serves the purpose of providing proper rigidity to the membrane 4 in the longitudinal direction, permitting it to be inserted through the mouth 7a of the cannula 7 into the artery 2. The wall thickness of the membrane 4 is, preferably, for example, between 2 and 2.5 mils, which assures good gas diffusibility and still provides adequate catheter lumen rigidity. A membrane exposed length of 5 inch beyond the end of the tubular portion 7b of cannula 7 provides a combined lumen volume of approximately 16 microliters for gas diffusion. It will be understood that in substitution for the U-shaped tube 5 alternative means can be employed for connecting lumens 4a, 4b at their distal ends such as, for example, providing one or more perforations in the web between them.

At their proximal ends the lumens 4a, 4b, respectively, accommodate a pair of metal connector tubes 27, 28 having inner diameters of, say 0.011 inch, and outer diameters of 0.013 inch, which pass through a bore along the axis of the shank 8a and one arm 8c of a Y-shaped hub 8, which may, for example, be molded from acetal plastic or the like. The tubes 27, 28 which extend from the end of shank 8a to about ⅛ inch beyond the end of arm 8c are press-fit into the axial bore, and sealed into position by, for example, a silicone adhesive. The male connector 8a of the hub is of a form known in the art as a "Luer taper." The male connector 8a provides a quick leak-proof connection to the mouth 7a of cannula 7. The female leg 8b communicates via a separate passage through male connector 8a with the blood surrounding the membrane portion 4 inside the cannula 7, thus providing a port for taking blood samples without disturbing the catheter.

The connecting tubes 27, 28 are joined beyond the end of adapter branch 8c to the respective tubular members 11, 12, each having respective inner diameters of 0.013 inch and 0.022 inch, which are formed of a material substantially non-diffusible, that is, impermeable, to gases such as, for example, stainless steel.

A cylindrical hole in the end of the branch 8c houses the distal end of an electrically insulated heater wire loop 13 which is cemented or otherwise secured into hub 8. The heater loop 13 and the tubes 11 and 12 are jacketed in an insulating outer tube 14 of, for example, polyvinyl chloride, which extends 5 or 6 feet beyond the end of hub 8, terminating in a receptacle and plug 9. The latter, which may also be of acetal plastic or another non-toxic insulating material, increases conically from a diameter just exceeding that of the connecting tube 14 to an enlarged diameter as shown in end view of FIG. 4. The end of plug 9 has two female connectors 15 and 16 at the emergent ends of the tubes 11 and 12 arranged adjacent a pair of male plugs which are extensions 13a, 13b of the two ends of heater wire loop 13. When the plug 9 is connected into a blood gas analysis system of the type disclosed in application Ser. No. 493,938 of U. Sielaff, W. R. Peickert and D. Brinkman, filed on Aug. 1, 1974, now abandoned and continuation application Ser. No. 593,606, filed on the aforenamed application on July 7, 1975, now U.S. Pat. No. 3,983,864, the supply gas tube 12 will be connected in continuous circuit relation to the carrier gas source, and the return gas tube 11 will be connected in circuit relation to the chromatographic analyzer.

Also, when plug 9 is connected into the system, the terminals 13a, 13b of heater wire 13 are connected to a conventional controlled source of power (not shown). The heater wire 13 preferably comprises an alloy of nickel or other high resistance wire, of sufficient resistance per unit length so that when connected to the source of power the gases in the connecting tubes 11 and 12 within the insulating jacket 14 are maintained at a uniform temperature in excess of 98.6° F (body temperature) preferably within the range 105° to 115° F, while the sample is in transition between the permeable membrane and the chromatographic analyzer.

Referring now specifically to FIGS. 6 through 9 of the drawing, there is shown a modified embodiment of the catheter of the present invention in which the distal end of catheter 101 comprises an external tubular membrane 104 surrounding a longitudinally-disposed non-diffusible internal return tube 118. In order to simplify the description, elements of the present embodiment similar to those described on the embodiment of FIG. 1 et seq., are designated by corresponding numbers to which 100 has been added. Tubular membrane 104, as in the embodiment previously described, is a gas permeable membrane, which may alternatively be defined as a semi-permeable membrane diffusible to gases but substantially indiffusible to liquids, such as blood. One example of a material useful for the purposes of the present invention is a methyl-vinyl-polysiloxane polymer with fumed silica filler, for rigidity. For the purposes of the present embodiment, the wall thickness of tube 104 is between 2 and 2.5 mils thick. It will be understood that the criteria for selecting semi-permeable membrane material are the same as those described with reference to the previous embodiment.

Tubular membrane 104, which is 0.028 inch outer diameter and 0.024 inch in inner diameter, and say 3.2 inch long is held rigidly in shape by means of an interposed coil 106 formed in the present embodiment of 330 turns of 2 mil diameter stainless steel wire. (See FIG. 9.) Coil 106 extends to within 0.010 inch of the distal end of tubular membrane 104, which is sealed gas tight by means of a plug 105 formed from acetoxysilane adhesive, known by the trademark R.T.V. SILICONE. The turns at the distal end of coil 106 are soldered in place in a bed of solder 121. At the proximal end, a short stainless steel sleeve 103, which is 0.20 inch in axial length, 0.021 inch in outer diameter, and 0.014 inch in inner diameter, is interposed for a length of 0.070 inch into the mouth of stainless steel coil 106, the latter being soldered in place against the outer periphery of the former for a length of 0.060 inch. A stainless steel return gas tube 118, 5½ to 6 feet long, having an outer diameter of 0.011 inch, and an inner diameter of 0.008 inch, is soldered to the inner wall of the sleeve 103, so that the distal end protrudes along the interior of tubular membrane 104 to within 0.020 inch of the inside face of plug 105, being soldered in place to the interior of supporting coil 106. The return tube 118 has a substantially circular opening 118a in the lateral wall, roughly 0.006 inch in diameter centered about 0.100 inch from its distal end, to facilitate the intake of return gas.

A 0.060 inch length at the proximal end of the sleeve 103 is joined in underlapping relation to the end of conduit 117 formed of trifluorochloroethylene (known by the trademark KEL-F). A gas-tight seal 119 formed from acetoxysilane adhesive, known by the trademark R.T.V. SILICONE surrounds a portion of 103, filling in the gap between the proximal end of membrane 104 and the distal end of conduit 117.

Referring again to FIG. 6, it is seen that the return gas tube 118 and the enclosing conduit 117 pass through the hollow distal leg 107b of cannula 107, which is 0.033 inch in inner diameter, and 0.047 inch in outer diameter, and substantially similar in form to cannula 7 described with reference to the previous embodiment. The mouth 107a of cannula 107 accommodates the hollow male connector 108a of the hub 108, which is similar to the form previously described, except that instead of a pair of parallel bores it has a bore designed to accommodate carrier gas supply conduit 117 enclosing stainless steel return gas tube 118. A cylindrical cavity 108d in the hub 108 provides an internal terminal receptacle including adapter 120 of flexible crossover tubing (which may be polyvinylchloride) for a connection between the enclosing plastic sleeve 117 and helium supply tube 112, and between gas return tube 118 and return connecting tube 111. The connections inside of cavity 108d are held in place with epoxy, which, when cured, renders the junctions gas-tight.

As in the previous embodiment, the female leg 108b provides communication by means of a separate passage through 108a with blood surrounding tubular membrane 104, inside of cannula 107, so that blood samples can be derived without disturbing the catheter.

Connecting tubes 111 and 112 are of material non-diffusible, that is, impermeable to gases, such as, for example, stainless steel, and are preferably of similar lengths and dimensions described with reference to the previous embodiment. Tubes 111 and 112 pass through the connector 108c and into the insulating outer sheath 114 of, for example, polyvinylchloride, which, as in the previous embodiment, extends 5 or 6 feet beyond the connector 108c terminating in receptacle and plug 109 which is similar in structure to plug 9 previously described with reference to FIG. 1, et seq.

As in the previous embodiment, the present embodiment also includes a heater loop 113, a portion of which is included in the epoxied area of the cavity 108d. The heater wires 113a and 113b pass along the conduit 114 in substantially parallel relation to tubes 111 and 112. When plug 109 is connected into the system, prongs 113a and 113b are connected to a conventional power source (not shown). The heater 113 maintains the gases in the conduits 111 and 112 at a uniform temperature exceeding body temperature, preferably within the range 105°–115° F while the sample derived from equilibration through the tubular membrane 104 is in transit to the chromatographic analyzer.

Although helium is the preferred carrier gas for the purposes of the present invention, it will be understood that the disclosed catheter is constructed for use with other carrier gases.

It will be understood that the scope of the blood gas catheter of this invention is not limited to the particular forms or materials disclosed herein, by way of example, but only by the scope of the appended claims. For example, although a tri-lumen membrane has been disclosed for ease of description of the first embodiment, it will be understood that the membrane is not necessarily limited to three lumens, but may comprise alternative designs, for example, having a large number of lumens or passages all inter-connected to form a single passage. Persons skilled in the art may also contemplate variations of the second disclosed embodiment, within the scope of the appended claims, in which the non-diffusible return tube is disposed in coaxial relation to the gas diffusible membrane tube.

We claim:

1. A device for sampling gases dissolved in the blood of a living subject, comprising in combination:
    a catheter having distal and proximal ends,
    means disposed at the distal end of said catheter comprising a tubular gas permeable membrane primarily of material highly permeable to gas but substantially impermeable to blood, constructed for insertion through a cannula percutaneously into the blood vessel in a direction extending along the principal axis thereof, said tubular membrane including a continuous gas permeable conduit, at least a portion of the lateral walls of said conduit being constructed and arranged during percutaneous deposition of said tubular membrane to make contact with the blood of said subject,
    means comprising a housing at the proximal end of said catheter including input and output gas receptacles respectively constructed and arranged for connection in circuit relation to a source of carrier gas at said input receptacle and to gas receiving means at said output receptacle,
    said conduit having input and output terminals respectively connected through separate connecting means to said input and output gas receptacles.

2. The combination in accordance with claim 1 wherein R, the permeability of said gas permeable membrane, is at least of the same order of magnitude as the permeability for oxygen through dimethyl silicone.

3. The combination in accordance with claim 1 wherein said gas permeable membrane consists essentially of a polysiloxane polymer.

4. A catheter in accordance with claim 1 wherein said gas permeable conduit has a substantially uniform cross-section and permeability along its length between said terminals.

5. The combination in accordance with claim 1 wherein said tubular gas permeable membrane comprises a plurality of lumens interconnected to form said continuous gas permeable conduit of substantially uniform cross section and permeability between said input and output terminals which is constructed and arranged to have a length in contact with the blood during said percutaneous disposition which substantially exceeds the length of the said tubular membrane.

6. The combination in accordance with claim 5 wherein said tubular gas permeable membrane comprises at least two substantially parallel lumens of substantially uniform cross section and permeability forming said gas permeable conduit substantially double the length of said membrane and joined together near the distal end of said catheter to provide a reversal of the direction of gas flow from one to the other, the opposite ends of said lumens respectively comprising said input and output terminals.

7. The combination in accordance with claim 6 wherein said tubular gas permeable membrane has an overall cross-sectional dimension not exceeding about 0.028 inch, and each of said lumens has an internal diameter not exceeding about 0.011 inch.

8. The combination in accordance with claim 5 comprising a stiffening wire interposed into an additional lumen in said tubular gas permeable membrane in substantially fixed position and extending substantially parallel to the length of said membrane.

9. The combination in accordance with claim 1 wherein said separate connecting means comprise a pair of tubes substantially impermeable to gas connected in mating relation between the input and output terminals of said tubular gas permeable conduit and the housing at the proximal end of said catheter.

10. The combination in accordance with claim 9 wherein said tubes substantially impermeable to gas consist essentially of stainless steel.

11. The combination in accordance with claim 1 wherein said tubular gas permeable membrane is in the form of a sleeve surrounding a return gas tube substantially impermeable to gas, said tubes and said sleeve being internally interconnected near the distal end of said catheter, said sleeve connected at its proximal end to said input terminal, and said substantially impermeable return gas tube connected at its proximal end to said output terminal.

12. The combination in accordance with claim 11 wherein supporting means comprising a coil of wire is interposed into said sleeve extending along the length of said sleeve and surrounding said substantially impermeable return gas tube.

13. A device for sampling gases dissolved in the blood of a living subject comprising in combination:
a catheter having distal and proximal ends,
means disposed at the distal end of said catheter comprising a tubular membrane primarily of gas permeable material constructed for insertion through a cannula percutaneously into the blood vessel in a direction extending along the principal axis thereof, said tubular membrane including a continuous gas permeable conduit, at least a portion of the lateral walls of said conduit being constructed and arranged in percutaneous disposition of said tubular membrane to make contact with the blood of said subject,
means comprising a housing at the proximal end of said catheter including input and output gas receptacles respectively constructed and arranged for connection in circuit relation to a source of carrier gas at said input receptacle and to gas receiving means at said output receptacle,
said conduit having input and output terminals respectively connected through separate connecting means to said input and output gas receptacles,
said separate connecting means comprising a pair of tubes substantially impermeable to gas connected in mating relation between said input and output terminals and said corresponding input and output gas receptacles of said housing, and
heating means in the form of at least one high-resistance wire loop extending substantially the length of the tubes of said pair and connected to a source of power, for maintaining the gases in said tubes at a temperature at least exceeding body temperature.

14. A device for sampling gases dissolved in the blood of a living subject comprising in combination:
a catheter having distal and proximal ends,
means disposed at the distal end of said catheter comprising a tubular membrane primarily of gas permeable material constructed for insertion through a cannula percutaneously into the blood vessel in a direction extending along the principal axis thereof, said tubular membrane including a continuous gas permeable conduit, at least a portion of the lateral walls of said conduit being constructed and arranged during percutaneous disposition of said tubular membrane to make contact with the blood of said subject,
means comprising a housing at the proximal end of said catheter including input and output gas receptacles respectively constructed and arranged for connection in circuit relation to a source of carrier gas at said input receptacle and to gas receiving means at said output receptacle,
said conduit having input and output terminals respectively connected through separate connecting means to said input and output gas receptacles,
said separate connecting means comprising a pair of tubes substantially impermeable to gas, and
an adapter hub having a male taper constructed to fit concentrically into the mouth of said cannula when the same is interposed into the blood vessel of the said subject, said male taper including a first passage constructed to surround and secure connections to the proximal end of said gas permeable membrane adjacent the junction with said substantially gas-impermeable tubes, and said male taper including a second passage substantially parallel to said first passage constructed to lead directly through the open end of said cannula at its distal end and terminating in a female taper at its proximal end, whereby said second passage is adapted to tap directly into the bloodstream of the said subject for drawing a blood sample without disturbing the position of the said catheter when interposed in a blood vessel.

15. A device for contacting the blood of a subject to remove gases from the blood, comprising in combination:
a catheter having distal and proximal ends,
said catheter comprising an inlet flow path means for introducing a carrier gas to the distal end of said catheter and an outlet flow path means for removing said carrier gas from the distal end of said catheter,
a portion of at least one of said flow path means comprising a membrane material highly permeable to gas but impermeable to blood, said portion constructed and arranged when in contact with the blood of said subject for allowing equilibration through the lateral wall thereof between said gases in the blood and the carrier gas passing along said at least one flow path means whereby gases in the blood enter said at least one flow path means and are mixed with the carrier gas, and the mixed gases are removed in said outlet flow path means.

16. A catheter as set forth in claim 15 wherein said portion of at least one of said flow path means comprises a portion of both said inlet flow path means and said outlet flow path means.

17. A catheter as set forth in claim 15 wherein said inlet flow path means and said outlet flow path means are elongated, capillary paths extending substantially along the length of the catheter.

18. A catheter as set forth in claim 15 wherein said membrane material is silicone polymer having a thickness of between 0.002 and 0.0025 inches.

* * * * *

UNITED STATES PATENT AND TRADEMARK OFFICE
CERTIFICATE OF CORRECTION

PATENT NO. : 4,016,864
DATED : April 12, 1977
INVENTOR(S) : Ulrich Sielaff and Wilfried R. Peickert It is certified that error appears in the above-identified patent and that said Letters Patent are hereby corrected as shown below:

Col. 8, line 4, "deposition" should be -- disposition --.

Signed and Sealed this sixteenth Day of August 1977

[SEAL]

Attest:

RUTH C. MASON
*Attesting Officer*

C. MARSHALL DANN
*Commissioner of Patents and Trademarks*